(12) United States Patent
Seelye et al.

(10) Patent No.: US 7,402,689 B2
(45) Date of Patent: Jul. 22, 2008

(54) VINYLCHLOROFORMATE-FREE SYNTHESIS OF VINYL AND ALLYL(THIO) CARBAMATES

(75) Inventors: David E. Seelye, Rochester, NY (US); Jay F. Kunzler, Canandaigua, NY (US); Joseph C. Salamone, Fairport, NY (US)

(73) Assignee: Bausch & Lomb Incorporated, Rochester, NY (US)

( * ) Notice: Subject to any disclaimer, the term of this patent is extended or adjusted under 35 U.S.C. 154(b) by 480 days.

(21) Appl. No.: 11/045,017

(22) Filed: Jan. 27, 2005

(65) Prior Publication Data

US 2005/0176980 A1   Aug. 11, 2005

Related U.S. Application Data

(60) Provisional application No. 60/540,134, filed on Jan. 28, 2004.

(51) Int. Cl.
*C07F 7/10* (2006.01)
(52) U.S. Cl. ..................................................... 556/420
(58) Field of Classification Search ............... 556/420
See application file for complete search history.

(56) References Cited

U.S. PATENT DOCUMENTS

| 5,070,215 | A | | 12/1991 | Bambury et al. |
| 5,218,133 | A | * | 6/1993 | Pepe et al. ............... 556/420 |
| 5,310,779 | A | | 5/1994 | Lai |
| 5,449,720 | A | | 9/1995 | Russell-Jones et al. |
| 5,512,205 | A | | 4/1996 | Lai |
| 5,610,252 | A | | 3/1997 | Bambury et al. |
| 5,914,355 | A | | 6/1999 | Kunzler |
| 6,153,760 | A | | 11/2000 | Kunzler |
| 6,166,236 | A | | 12/2000 | Bambury et al. |
| 2002/0151740 | A1 | | 10/2002 | Allen et al. |

FOREIGN PATENT DOCUMENTS

| WO | WO 01/00634 | 1/2001 |
| WO | PCT/ISA210 | 6/2005 |

* cited by examiner

*Primary Examiner*—Peter O'Sullivan
(74) *Attorney, Agent, or Firm*—Glenn D. Smith

(57) ABSTRACT

The invention generally relates to methods of forming vinyl (thio)carbamates and more particularly to a vinylchloroformate-free method of synthesizing (N-vinyloxycarbonyl)-3-aminopropyltris(trimethylsiloxysilane).

24 Claims, No Drawings

VINYLCHLOROFORMATE-FREE SYNTHESIS OF VINYL AND ALLYL(THIO) CARBAMATES

This application claims benefit of priority of Provisional U.S. Patent Appln. No. 60/540,134, filed Jan. 28, 2004, the contents of which are incorporated by reference herein.

BACKGROUND AND SUMMARY

The invention generally relates to methods of forming vinyl or allyl(thio)carbamates and more particularly to a vinylchloroformate-free method of synthesizing (N-vinyloxycarbonyl)-3-aminopropyltris(trimethylsiloxysilane).

Two of the key monomers used in the production of hydrogel contact lenses are (N-vinyloxycarbonyl)-3-aminopropyltris(trimethylsiloxysilane) (RD325) and vinylcarbamate-capped polydimethylsiloxane (RD352). The current synthesis of RD325 consists of reacting vinylchloroformate (VCF) with aminopropyltris(trimethylsiloxysilane). The current synthesis of RD352 involves a triflic acid catalyzed ring opening polymerization of octamethylcyclotetrasiloxane with a vinyl carbamate butyl-capped tetramethyldisiloxane (V2). V2 is prepared by the reaction of VCF with 1,3-(4-hydroxybutyl)-1,1,3,3-tetramethyldisiloxane. Both syntheses are relatively straightforward and result in a high yield of product. A significant drawback, however, of both reactions is that the monomer VCF is used.

Vinylchloroformate is a monomer used in various applications such as, for example, the making of contact lenses. Currently, it is believed that this compound is only available via a multi-step synthesis typically involving the use of phosgene and organomercury intermediates. These intermediates are undesirable in that they present heightened environmental concerns.

Alternative methods for making vinyl carbamates have been developed. For example, U.S. Pat. No. 6,423,862 discloses a multistep method for making a vinyl carbamate that does not necessitate the use of phosgene and organomercury intermediates. However, additional methods of making vinyl or allyl(thio)carbamates that do not require the use of phosgene and organomercury intermediates and are relatively straightforward are still needed.

The present invention addresses the above shortcomings and provides methods for making vinyl or allyl(thio)carbamates that do not necessitate the use of phosgene and organomercury intermediates. In one aspect, the invention provides a method for making a vinyl or allyl(thio)carbamate siloxy compound represented by the formula (I):

$$(CH_2=CH(CH_2)b\text{-}Y\text{---}C(O)N)_xR_1 \quad (I)$$

wherein x is 0 or 1, b is 0 or 1, Y is O or S and $R_1$ is an organic siloxy containing radical.

Preferably $R_1$ is a mono-functional organic siloxy containing radical having the formula

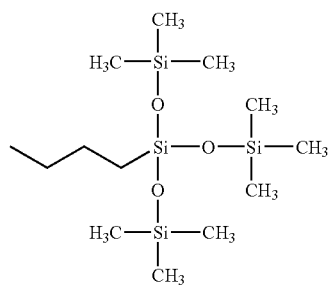

or a di-functional organic siloxy containing radical having the formula

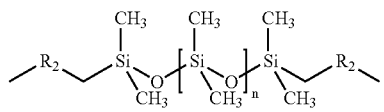

wherein $R_2$ is alkyl, alkyl ether or haloalkyl and n is 1-150. It should be recognized that the N-propyltris(trimethylsiloxysilane) radical and the difunctional radical are simply preferred embodiments. For example, when the alkyl portion of this radical is present it may be from 1 to 20 carbons in length and the methyl groups present on the mono- or di-functional siloxy containing radical may be partially or completely substituted with, for example, fluorine atoms or a fluorinated side chain radical. Such variations in the initial reactants are within the purview of one of ordinary skill in the art. Preferably, the compound represented by formula (I) is a trisiloxysilane vinylcarbamate in which instance b is 0, Y is O and $R_1$ is a substituted or unsubstituted trisiloxysilane group. Alternatively, the compound represented by formula (I) is a vinyl or allyl (thio)carbamate-capped polysiloxane.

The method comprises:

(a) reacting a compound represented by formula (II):

$$CH_2=CH(CH_2)_b OSi(CH_3)_3 \quad (II)$$

wherein b is 0 or 1, with a compound represented by formula (III):

$$(Y=C=N\text{---}(CH_2)_m)_x\text{---}R1 \quad (III)$$

wherein x is 0 or 1, Y is O or S, m is 0 to 20 and $R_1$ is an organic siloxy containing radical to form the compound of formula (I):

$$(CH_2=CH(CH_2)_b YC(O)N)_x R_1 \quad (I)$$

wherein x is 0 or 1, b is 0 or 1, Y is O or S and $R_1$ is a mono- or di-functional organic siloxy containing radical.

DETAILED DESCRIPTION OF THE PREFERRED EMBODIMENTS

As used herein, the expression "vinyl or allyl(thio)carbamates" refers to vinylcarbamates and allylcarbamates that may optionally contain a sulfur atom in place of the ether oxygen in a carbamate portion of the compound.

As used herein, the expression "substantially pure" is used to describe the purity of the final product having not more than about 3% of impurities present in the final product provided by the invention herein.

The invention will now be described with respect to certain embodiments described herein. It should be appreciated however that these embodiments are for the purposes of illustrating the invention and are not to be construed as limiting the scope of the invention as defined by the claims.

An example of a synthetic scheme for producing vinyl carbamates in accordance with the invention is as follows wherein $R_1$ is a mono- or di-functional organic siloxy containing radical:

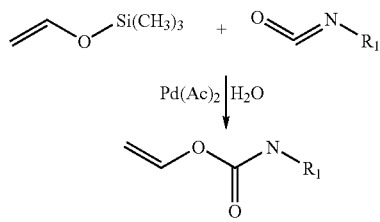

When the desired final compound is an N-propyltrisiloxysilane vinylcarbamate the method comprises the following reaction route:

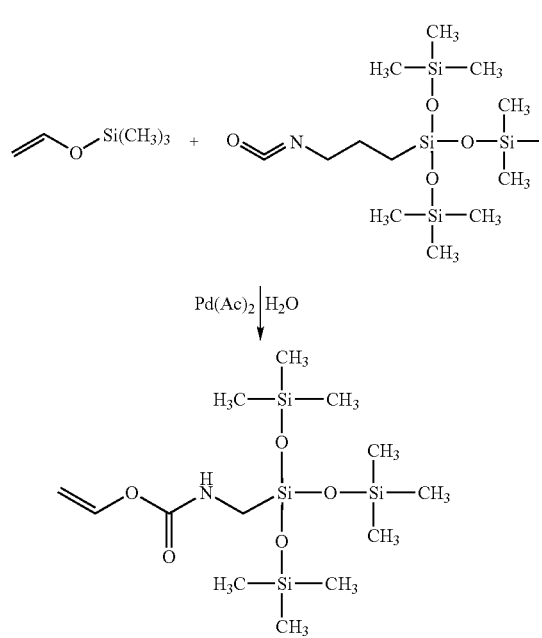

This invention also discloses a novel method for making vinyl or allyl(thio)carbamate capped macromonomers that utilize the isocyanate/siloxysilane reaction route set forth above. The synthetic concept of this invention can be utilized to prepare a wide variety of vinyl or allyl(thio)carbamate functionalized macromonomers, including, but not limited to, block copolymers, star and graft copolymers and mono-functionalized macromonomers. For example, it can be applied to the synthesis of vinyl carbamate capped polysiloxanes. The general synthetic route for this macromonomer is shown below:

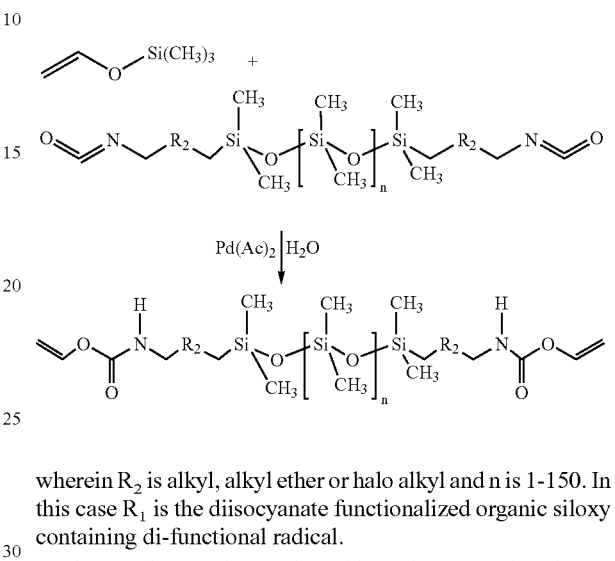

wherein $R_2$ is alkyl, alkyl ether or halo alkyl and n is 1-150. In this case $R_1$ is the diisocyanate functionalized organic siloxy containing di-functional radical.

The reaction can be conducted in various organic solvents such as are known to those skilled in the art. Exemplary organic solvents include, for example, polar aprotic solvents such as dimethyl formamide ("DMF"), acetonitrile, dimethyl sulfoxide ("DMSO"), dimethylacetamide and the like. Non-polar organic solvents can also be used such as hexane, heptane, toluene, cyclohexane, and the like, along with ether-like solvents such as, but not limited to, diethyl ether, tetrahydrofuran ("THF"), methyl-t-butyl ether (MTBE), the glymes, and the like. Combinations of any of these solvents may be used.

Various catalysts can be used and include those known to those of skill in the art. Non-limiting examples of suitable catalysts and solvents that have proven useful in the reaction of the invention herein are disclosed in Table 1 below. The samples were prepared according to the general method set forth in Example 1 below with the catalyst and solvent being varied as indicated in Table 1.

TABLE 1

| Sample | catalyst | moles cat. | solvent | time | % Product (RD325) |
|---|---|---|---|---|---|
| 1 | Copper powder | 18.40% | NMP | 20 hrs | 12.4 |
| 2 | tk(tpp)pd 21,666-6 | 1.08% | NMP | 20 hrs | 19.2 |
| 3 | tk(tpp)pd 21,666-6 | 1.08% | DMF | 20 hrs | 21.3 |
| 4 | PdAc2 | 5.18% | THF | 20 hrs | 67.8 |
| 5 | PdAc2 | 5.18% | glyme | 20 hrs | 54.2 |
| 6 | PdAc2 | 5.18% | 1,4-dioxane | 20 hrs | 31.9 |
| 7 | PdAc2 | 5.18% | EtOAc | 20 hrs | 57.7 |
| 8 | PdAc2 | 5.18% | NMP | 20 hrs | 46.6 |
| 9 | PdAc2 | 5.18% | neat | 20 hrs | 23.1 |
| 10 | PdAc2 | | DMF | 20 hrs | 29.7 |
| 11 | PdAc2 | | DMA | 20 hrs | 71.4 |
| 12 | PdAc2 | | CHCN | 20 hrs | 17.8 |
| 13 | PdAc2 | | 2-imidazolid | 20 hrs | 77.7 |
| 14 | PdAc2 | | Et2O | 20 hrs | 14.4 |
| 15 | Copper (I) iodide | 6.10% | NMP | 20 hrs | 14.8 |
| 16 | Ptacac | 3.42% | 1,4-dioxane | 20 hrs | 14.4 |

TABLE 1-continued

| 17 | DS255 | 2.80% | NMP | 20 hrs | 11.6 |
|---|---|---|---|---|---|
| 18 | PtCl2 | 4.37% | 1,4-dioxane | 20 hrs | 28.7 |
| 19 | PdCl2 | 6.50% | 1,4-dioxane | 20 hrs | 12.6 |
| 20 | bis(benzo 22,368-9 | | 1,4-dioxane | 20 hrs | 22.6 |
| 21 | Cd | | NMP | 20 hrs | 10.9 |
| 22 | Silver (II) Acetate | | NMP | 20 hrs | 10.7 |
| 23 | tktppPd(O) 21,666-6 | | NMP | 20 hrs | 24.9 |
| 24 | tktppPt (O) 24,496-1 | | NMP | 20 hrs | 18.2 |
| 25 | PtO2 20,603-2 | | NMP | 20 hrs | 15.8 |
| 26 | PdTFA2 | | glyme | 20 hrs | 19.8 |
| 27 | PdTFA2 | | 1,4-dioxane | 20 hrs | 26.2 |
| 28 | PdTFA2 | | EtOAc | 20 hrs | 27.9 |
| 29 | PdTFA2 | | NMP | 20 hrs | 26 |
| 30 | Pt(0) 1,3-divinyl | | EtOAc | 20 hrs | 11.3 |
| 31 | Pt(0) 1,3-divinyl | | NMP | 20 hrs | 14.8 |
| 32 | Rubidium Acetate | | NMP | 20 hrs | 10.7 |
| 33 | CuBr2 | | NMP | 20 hrs | 14.1 |

KEY

| tk(tpp)pd 21,266-6 | tetrakis(triphenylphosphine)palladium (0) |
|---|---|
| DS255 | 1,10-Phenanthroline Platinum diacetate (in house synthesis) |
| bis(benzo 22,368-9 | bis(benzonitrile)palladium (II)chloride |
| tktppPd(O)21,266-6 | tetrakis(triphenylphosphine)palladium(0) |
| tktppPt(O)24,496-1 | tetrakis(triphenylphosphine)platinum (0) |
| PtO2 20,603-2 | Platinum oxide |
| PdTFA2 | Palladium (II) trifluoroacetate |
| Pt(O) 1,3-divinyl | Platinum (0) 1,3-divinyl-1,1,3,3-tetramethyldisiloxane complex in xylene |
| 2-imidazolid | 2-imidazolidone |
| PdAc2 | Palladium (II) acetate |
| Ptacac | Platinum acetylacetonate |

The invention will be better understood by way of the following examples that are intend to illustrate, but not limit, the claims attached hereto. Abbreviations used herein are as follows:

| (RD325) | N-vinyloxycarbonyl-3-aminopropyltris(trimethylsiloxysilane) |
|---|---|
| (NMP) | N-methyl-2-pyrrolidone |
| (DMF) | Dimethyl furamide |
| (Et2O) | Diethyl ether |
| (EtOAc) | Ethyl acetate |
| (THF) | Tetrahydrofuran |
| (Glyme) | Ethylene glycol dimethyl ether |
| (CHCN) | Acetonitrile |
| (GFF) | Glass fiber filter |
| (TMS) | Trimethylsilane |
| PdAc2 | Palladium (II) acetate |

EXAMPLE 1

A mixture of isocyanopropyltris(trimethylsiloxy) (2.5 g, 0.66 mmole), trimethyl(vinyloxy)silane (2.3 g, 20 mmole), water (0.2 g, 0.011 mole) and Pd(Ac)$_2$ (0.05 g, $2.2 \times 10^{-4}$ mole) was dissolved in dimethylacetamide (20 mL) and heated to 60° C. The reaction was complete following 20 hours of heating as shown by GC (98% RD325 with only 1.5% unreacted isocyanate). The reaction solution was then filtered through a diatomaceous earth/MgSO$_4$/Silica cake using a GFF filter. The solution was dissolved in heptane, washed with 2$\underline{N}$ HCl, dried over MgSO$_4$ and vacuum stripped. The resultant RD325 (structure confirmed by GC-MS) was 98% pure by GC and can be used as a device forming comonomer without additional column purification.

EXAMPLE 2

Into a 5000 mL 3-neck round bottom flask that has been acid washed and fitted with a mechanical stirrer, heating mantle and thermometer was added 1.1 g of Pd(Ac)$_2$ and 1950 mL of dimethylacetamide. To this was added 500 g of tris(trimethylsilane)-N-propylsilane isocyanate and 250 g of CH$_2$=CHO-TMS. The mixture was stirred for 45 minutes as the temperature was brought to 30° C. 23.46 g of reverse osmosis water was added to the reaction mixture over 35 minutes. After the addition of the water, the mixture was maintained at 47° C. for 30 minutes. The heating mantle was turned off, and the reaction mixture was allowed to cool for 5 hours.

The reaction mixture was dried by serial additional of magnesium sulfate with filtering after each addition of magnesium sulfate. The filtrate was placed in a separatory funnel along with 1000 mL of heptane. The organic mixture was washed with 1000 mL of ice cold 0.5 $\underline{N}$ HCl. The first aqueous layer was back washed with 500 mL of heptane. The combined organics were then washed with 500 mL of 2$\underline{N}$ HCl and then 500 mL of deionized water. The organics were dried with magnesium sulfate and 10 g silica gel. The mixture was filtered and transferred to a flask with a magnetic stirrer. While stirring, 40 g of silica gel was slowly added to the organics and the mixture was allowed to dry. After drying, the mixture was filtered and the solvent was flash evaporated. Remaining solvent was removed under vacuum leaving the product behind as a light yellow oil.

The examples and comparative examples set forth in Table 2 below were prepared according to the procedure set forth in Example 1 with use as the reactants those compounds listed as the heading in the rows and columns. The yield of the desired monomer is provided in weight percent. NP indicates that the listed reaction was not performed.

TABLE 2

| | CH$_2$=CH-O-Si(CH$_3$)$_3$ | CH$_2$=CH-CH$_2$O-Si(CH$_3$)$_3$ | CH$_3$-C(=CH$_2$)-C(=O)-O-(CH$_2$)$_2$-O-Si(CH$_3$)$_3$ | (CH$_3$)$_3$Si-O-(1,3-cyclohexadienyl) | CH$_3$(CH$_2$)$_2$-O-Si(CH$_3$)$_3$ |
|---|---|---|---|---|---|
| Ph-N=C=O | <1% | <1% | N/P | N/P | N/P |
| Ph-N=C=S | <1% | <1% | N/P | N/P | N/P |
| Cy-N=C=O | <1% | <1% | N/P | N/P | N/P |
| O=C=N-(CH$_2$)$_5$CH$_3$ | 75% | N/P | 13.5% | 44.1% | 17.7% |
| S=C=N-(CH$_2$)$_5$CH$_3$ | 60% | 15% | N/P | N/P | N/P |

As shown in Table 2, the method of the invention herein may comprise, for example, making an allylcarbamate or an allyl thio carbamate, the method comprising: reacting N-hexylisocyanate with a compound selected from the group consisting of trimethyl(vinyloxy)silane, allyloxytrimethylsilane, 2-(trimethylsiloxy)ethyl methacrylate, 2-(trimethylsiloxy)-1,3-cyclohexadiene and trimethyl-N-propoxysilane to yield an allylcarbamate compound or reacting N-hexylisothiocyanate with a compound selected from the group consisting of trimethyl(vinyloxy)silane, allyloxytrimethylsilane, 2-(trimethylsiloxy)ethyl methacrylate, 2-(trimethylsiloxy)-1,3-cyclohexadiene and trimethyl-N-propoxysilane to yield an allylthiocarbamate compound.

The claims, as originally presented and as they may be amended, encompass variations, alternatives, modifications, improvements, equivalents, and substantial equivalents of the embodiments and teachings disclosed herein, including those that are presently unforeseen or unappreciated, and that, for example, may arise from applicants/patentees and others.

What is claimed is:

1. A method for making a compound represented by the following formula (I):

(CH$_2$=CH(CH$_2$)$_b$YC(O)N)$_x$R$_1$  (I)

wherein x is 0 or 1, b is 0 or 1, Y is O or S and R$_1$ is a mono- or di-functional organic siloxy containing radical, the method comprising:

reacting a compound represented by formula (II):

CH$_2$=CH(CH$_2$)$_b$OSi(CH$_3$)$_3$  (II)

wherein b is 0 or 1,
    with a compound represented by formula (III):

(Y=C=N—(CH$_2$)$_m$)$_x$—R1  (III)

wherein x is 0 or 1, Y is O or S, m is 0 to 20 and R$_1$ is a mono- or di-functional organic siloxy containing radical to provide the compound of formula (I).

2. The method of claim 1 wherein the compound of formula (I) is selected from the group consisting of vinylcarbamates, vinylthiocarbamates, allylcarbamates and allylthiocarbamates.

3. The method of claim 1 wherein the reaction takes place in the presence of a catalyst.

4. The method of claim 3 wherein the catalyst is selected from the group consisting of copper, copper (I) iodide, cadmium, silver (II) acetate, rubidium acetate, tetrakis(triphenylphosphine)palladium (0), 1,10-phenanthroline platinum diacetate, bis(benzonitrile)palladium (II)chloride, tetrakis(triphenylphosphine)palladium(0), tetrakis(triphenylphosphine)platinum (0), platinum oxide, palladium (II) trifluoroacetate, platinum (0) 1,3-divinyl-1,1,3,3-tetramethyldisiloxane complex in xylene, 2-imidazolidone, palladium (II) acetate and platinum acetylacetonate.

5. The method of claim 1 wherein the reaction takes place in the presence of a solvent.

6. The method of claim 5 wherein the solvent is an organic solvent.

7. The method of claim 6 wherein the organic solvent is a polar aprotic solvent.

8. The method of claim 7 wherein the polar aprotic solvent is selected from the group consisting of dimethyl formamide, acetonitrile, dimethyl sulfoxide, dimethylacetamide and mixtures thereof.

9. The method of claim 6 wherein the solvent is a non polar solvent.

10. The method of claim 9 wherein the non polar solvent comprises at least one member selected from the group consisting of hexane(s), heptane, toluene, cyclohexane, diethyl ether, tetrahydrofuran, methyl-t-butyl ether, glyme, and mixtures thereof.

11. The method of claim 1 wherein $R_1$ is a mono-functional organic siloxy-containing radical having the formula:

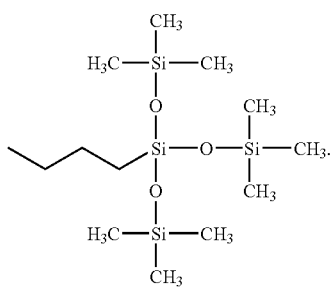

12. The method of claim 1 wherein $R_1$ is a di-functional organic siloxy-containing radical having the formula:

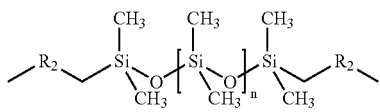

wherein $R_2$ is alkyl, alkyl ether or halo alkyl and n is 1-150.

13. A method of synthesizing vinyl carbamates comprising:
   providing a mixture of isocyanopropyl tris(trimethylsiloxy), trimethyl(vinyloxy)silane, water and catalyst;
   dissolving the mixture in an organic solvent to yield a reaction mixture; and
   subjecting the reaction mixture to reaction conditions suitable to yield a vinylcarbamate product.

14. The method of claim 13 further comprising the step of filtering the reaction mixture containing the vinylcarbamate product to remove the catalyst and provide a solution of the vinylcarbamate product in solvent.

15. The method of claim 14 further comprising the steps of
   washing the solution of vinylcarbamate product with a dilute acid solution;
   separating the solution of vinylcarbamate product from the dilute acid solution; and
   drying the solution of vinylcarbamate product to yield a substantially pure vinylcarbamate product.

16. A method of making an allylcarbamate, the method comprising:
   reacting N-hexylisocyanate with a compound selected from the group consisting of trimethyl(vinyloxy)silane, allyloxytrimethylsilane, 2-(trimethylsiloxy)ethyl methacrylate, 2-(trimethylsiloxy)-1,3-cyclohexadiene and trimethyl-N-propoxysilane to yield an allylcarbamate compound.

17. A method of making an allyl thio carbamate, the method comprising:
   reacting N-hexylisothiocyanate with a compound selected from the group consisting of trimethyl(vinyloxy)silane, allyloxytrimethylsilane, 2-(trimethylsiloxy)ethyl methacrylate, 2-(trimethylsiloxy)-1,3-cyclohexadiene and trimethyl-N-propoxysilane to yield an allylthiocarbamate compound.

18. The method of claim 1 wherein the compound represented by formula (I) is a trisiloxysilane vinylcarbamate wherein Y is O and $R_1$ is selected from the group consisting of organic siloxy-containing radicals comprising substituted or unsubstituted trisiloxysilane functional groups.

19. The method of claim 1 wherein the compound represented by formula (I) is a siloxysilane vinylcarbamate wherein Y is O and $R_1$ is selected from the group consisting of substituted trisiloxysilane groups, unsubstituted trisiloxysilane groups and vinylcarbamate capped polysiloxane groups.

20. The method of claim 1 wherein the compound represented by formula (I) is a vinyltrisiloxysilane thio carbamate wherein Y is S and $R_1$ is selected from the group consisting of organic siloxy-containing radicals comprising substituted or unsubstituted trisiloxysilane functional groups.

21. The method of claim 1 wherein the compound represented by formula (I) is a vinyltrisiloxysilane thiocarbamate in wherein Y is S and $R_1$ is selected from the group consisting of substituted trisiloxysilane groups, unsubstituted trisiloxysilane groups and vinylcarbamate capped polysiloxane groups.

22. The method of claim 1 wherein the compound made is (N-vinyloxycarbonyl)-3-aminopropyltris(trimethylsiloxysilane).

23. The method of claim 1 wherein the compound made is a vinylcarbonate capped polydimethylsiloxane.

24. A method of synthesizing vinyl carbamates comprising:
   providing a mixture of isocyanopropyl tris(trimethylsiloxy), trimethyl(vinyloxy)silane, water and palladium (II) acetate catalyst;
   combining the mixture with dimethylacetamide to yield a reaction mixture; and
   subjecting the reaction mixture to reaction conditions suitable to yield a vinylcarbamate product.

* * * * *